United States Patent [19]

Merrick

[11] 4,160,171

[45] Jul. 3, 1979

[54] METHOD AND APPARATUS FOR DETERMINING THE REFERENCE VOLTAGE IN AN IMPRESSED CURRENT CORROSION PROTECTION SYSTEM

[75] Inventor: Larry H. Merrick, Houston, Tex.

[73] Assignee: Harco Corporation, Medina, Ohio

[21] Appl. No.: 822,079

[22] Filed: Aug. 5, 1977

[51] Int. Cl.² .............................................. B01K 1/00
[52] U.S. Cl. .................................. 307/95; 204/195 C
[58] Field of Search ................ 307/95, 104; 204/196, 204/147, 195 C, 1 C; 363/44–48

[56] References Cited

U.S. PATENT DOCUMENTS

| | | | |
|---|---|---|---|
| 1,142,858 | 6/1915 | Tatum | 307/104 |
| 1,891,005 | 12/1932 | Neeley | 204/147 |
| 2,021,519 | 11/1935 | Polin | 204/196 |
| 2,176,514 | 10/1939 | Thomson | 204/147 |
| 2,332,955 | 10/1943 | Vautier | 264/176 R |
| 2,368,264 | 1/1945 | Scott | 320/21 |
| 2,584,816 | 2/1952 | Sands | 204/231 |
| 2,759,887 | 8/1956 | Miles | 204/196 |
| 2,982,714 | 5/1961 | Sabins | 204/196 |
| 2,986,512 | 5/1961 | Sabins | 204/196 |
| 2,987,461 | 6/1961 | Sabins | 204/196 |
| 2,998,371 | 8/1961 | Sabins | 204/196 |
| 3,129,154 | 4/1964 | Fry | 204/147 |
| 3,371,023 | 2/1968 | Banks | 204/147 |
| 3,375,183 | 3/1968 | Banks | 204/196 |
| 3,378,472 | 4/1968 | Banks | 204/147 |
| 3,634,222 | 1/1972 | Stephens | 204/196 |
| 3,641,420 | 2/1972 | Richman | 363/44 |
| 3,788,962 | 1/1974 | Frenck | 204/195 C |
| 3,953,742 | 4/1976 | Anderson | 307/95 |

*Primary Examiner*—L. T. Hix
*Assistant Examiner*—S. D. Schreyer
*Attorney, Agent, or Firm*—Pravel, Gambrell, Hewitt, Kirk, Kimball & Dodge

[57] ABSTRACT

Method and apparatus for determining the true cathode polarization potential or reference voltage for any corrosion protection system and which determination may be visually indicated, used as a feedback for automatic control of the corrosion protection system or both.

1 Claim, 6 Drawing Figures

METHOD AND APPARATUS FOR DETERMINING THE REFERENCE VOLTAGE IN AN IMPRESSED CURRENT CORROSION PROTECTION SYSTEM

CROSS REFERENCE TO RELATED APPLICATION

This application is related to our common assignee's co-pending application entitled "Cathodic Protection Method and Apparatus", Ser. No. 772,440, filed Feb. 28, 1977, now U.S. Pat. No. 4,080,272 and which is hereby totally incorporated herein by this reference for any and all purposes.

BACKGROUND OF THE INVENTION

This invention relates to the field of corrosion protection systems and method and in particular for determining the true polarization potential in the system.

Use of cathodic protection systems to protect a cathode metal in contact with an electrolyte fluid is well known. Generally, cathodic protection systems are of two types—sacrificial anode or impressed current systems.

The sacrificial anode system relies upon the natural difference in electrical potential between a cathode and an anode to sacrifice or consume the anode to protect the cathode. As such systems inherently rely upon the natural difference in potential there is no need to measure and compensate for changes in the electrical potential between the anode and cathode.

The latter type system—impressed current—is considered more reliable, and usually relies upon a rectifier means to supply an impressed electrical direct current between the anode and cathode, but other sources of direct current may be used. For examples of such other power sources, see *Control of Pipeline Corrosion* by A. W. Peabody, copyrighted 1967 by, and available from, the National Association of Corrosion Engineers, 2400 West Loop South, Houston, Tex. 77027.

Generally speaking, the direct current impressed current producing rectifiers are powered by either 3-phase or single-phase alternating current (hereinafter AC) that is usually reduced in voltage by a transformer before being rectified into a direct current (hereinafter DC) output of a desired type. Normally, electrical current rectification is done by either a selenium or silicon rectifying disc or diode element which is electrically connected with similar discs to attain the DC voltage output desired. The known output is a positive direct current voltage and amperage having a rippling wave form of some function such as full wave, of the alternating current input to the rectifier.

Impressed current systems may also be used in an anodic passivation system such as disclosed in Bank, et al, U.S. Pat. Nos. 3,378,472; 3,375,183; and 3,371,023.

Precise control of the impressed current in a cathodic protection system is not only highly desirable, but has become a prime requirement. Early impressed current cathodic protection systems, for instance that disclosed in U.S. Pat. No. 2,176,514, lacked means for adjusting the impressed current to a changing environment. If the impressed current used was less than that required by the system, the system was inadequate and the undesired corrosion resulted. If, on the other hand, the impressed current used exceeded the system requirements electrical power was wasted and, equally important, paint "blistering" or other damage to the cathode's protective coating would result.

Earlier attempts to solve those problems used precise electrical output apparatus such as that disclosed in U.S. Pat. Nos. 2,332,955; 2,584,816; and 2,368,264.

However, it was quickly recognized that the cathodic protection system reference or natural voltage varied in response to a number of unrelated factors, such as temperature and condition of the protective coating on the cathode, and which factors that were changing from time to time. To compensate for such changes the rectifier output of direct current was made adjustable. Some were manually adjustable as disclosed in Polis U.S. Pat. No. 2,021,519. Early examples of automatically adjusting cathodic protection systems are disclosed in U.S. Pat. Nos. 1,891,005; 2,759,887; and 3,143,670, while U.S. Pat. Nos. 1,142,858 and 1,438,946 disclose general purpose output self-adjusting electrical apparatus. This automatic control or adjustment has usually been achieved in the prior art using saturable reactor control or with a silicon controlled rectifier (hereinafter SCR). For additional information, see the August 1968 article at pages 26–29 of *Materials Protection*, available from the National Association of Corrosion Engineers at the above address. Generally, the output of direct current from said sources have been pulsating which has created an error indicating output in the reference voltage.

In U.S. Pat. Nos. 2,986,512, 2,982,714; 2,987,461; and 2,998,371, all to Sabins, there is disclosed a number of control systems for automatically controlling the impressed current rectifier output. Another example employing solid state transistors may be found in Andersen, et al, U.S. Pat. No. 3,953,742 or Rubelman U.S. Pat. No. 3,373,100.

U.S. Pat. No. 3,129,154 discloses a compensating method of controlling the impressed current in which a known electromotive force is made opposed to the unknown reference electromotive force. In such arrangement, the electrical current flow through the reference circuit is minimized and polarization of the reference electrode, as well as the resulting deterioration, is minimized. The continuous pulsing anode current flow through the reference electrode created a voltage due to the IR drop which tended to induce an error in the reference voltage determination.

U.S. Pat. No. 3,634,222 disclosed an improved cathodic protection automatic control system in which the true cathode polarization potential could be determined using the "instant off" method. In this patent, the apparent reference potential is said to consist of the true reference potential and three error components that are removed by turning the system off. By turning the protection system off, the IR voltage drop resulting from the impressed current flow was eliminated and the true reference voltage drop determined. While such system does eliminate some of the error in determining the true potential, the system employed a sequential controller that was subject to failure and periodically interrupted the operation of the cathodic protection of the system and thereby leaving the cathode unprotected.

The related application identified above discloses a system that is synchronized to determine the natural reference voltage during zero voltage periods between pulses of impressed current in the electrolyte. In three-phase alternating current input system such zero output periods do not exist and that system is not usable.

The preciseness of any automatic control system is dependent upon the quality of the reference voltage signal received for indicating the system condition. This is true whether or not the reference voltage signal is used in an automatic controller or is simply indicated.

SUMMARY OF THE INVENTION

The present invention relates to a new and improved method and apparatus for determining the true reference voltage in an impressed current corrosion protection system.

The system reference voltage is continuously sampling by a reference electrode half cell which produces an output signal having the true references voltage as well as the IR voltage drops resulting from the induced current. The reference output signal is reinforced and split into two processing channels. In a first channel the output signal is filtered through a capacitor to remove the relatively constant natural reference voltage direct current and pass the rapidly changing alternating current component produced by the IR voltage drop of the pulsating impressed current. The signal component having the natural reference voltage is further processed in the first channel to assure a polarity shift and then recombined with the signal in the second channel to cancel the alternating current component to produce a true polarization or reference voltage signal. The reference voltage signal may be indicated, used as a system automatic control feedback signal, or both.

BRIEF DESCRIPTON OF THE DRAWINGS

BRIEF DESCRIPTION OF THE PREFERRED EMBODIMENT

Figure 1:
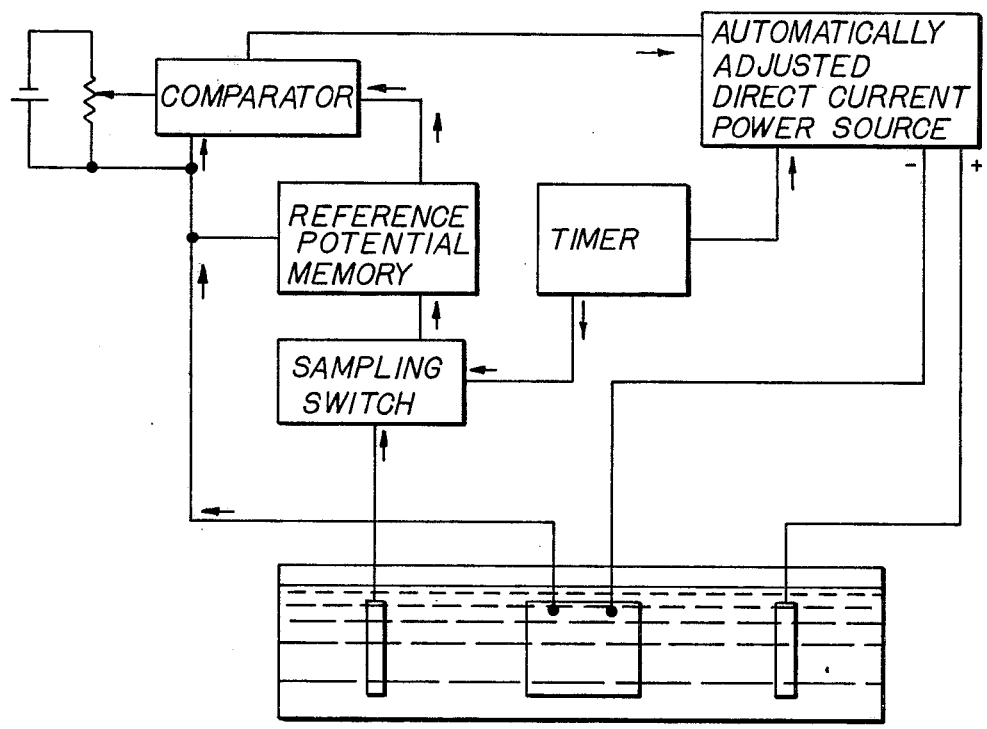
FIG. 1 is a schematic illustration of a prior art corrosion protection system.

FIG. 1 is a schematic illustration of a prior art corrosion protection system as represented by U.S. Pat. No. 3,634,222. In this prior art patent, a cyclic timer mechanism turns off the source of impressed direct current in the electrolyte, usually a form of AC-DC rectifier, for a period of time while the reference reading is made through a separate reference electrode disposed at a predetermined position in the electrolyte. As the reference electrode is used to provide an automatic feedback for automatic control of the output of the source of impressed direct current very precise determination of the reference voltage is a necessity. The purpose of the cyclic timer was to eliminate the induced current electrolyte IR errors while the true reference voltage was being read and thereby produce a true reference voltage or cathode polarization potential. Preferably, the sampling period was of a duration of 1.0 to 10.0 milliseconds during which time the corrosion protection induced current was absent and the protection system was not functioning.

This prior art was applicable to both single phase and three phase supply alternating current to the source of the impressed current. However, even interrupting the impressed current could not assure a precise determination, since strong voltages from other sources, such as a DC, return on an electric railroad or pipeline.

The present invention overcomes the difficulty of the prior art by eliminating all of the IR voltage drop resulting from the pulsing flow of impressed current and any stray current and enables the precise determination of the true reference voltage without the need to interrupt impressed current flow and corrosion protection.

Figure 2:
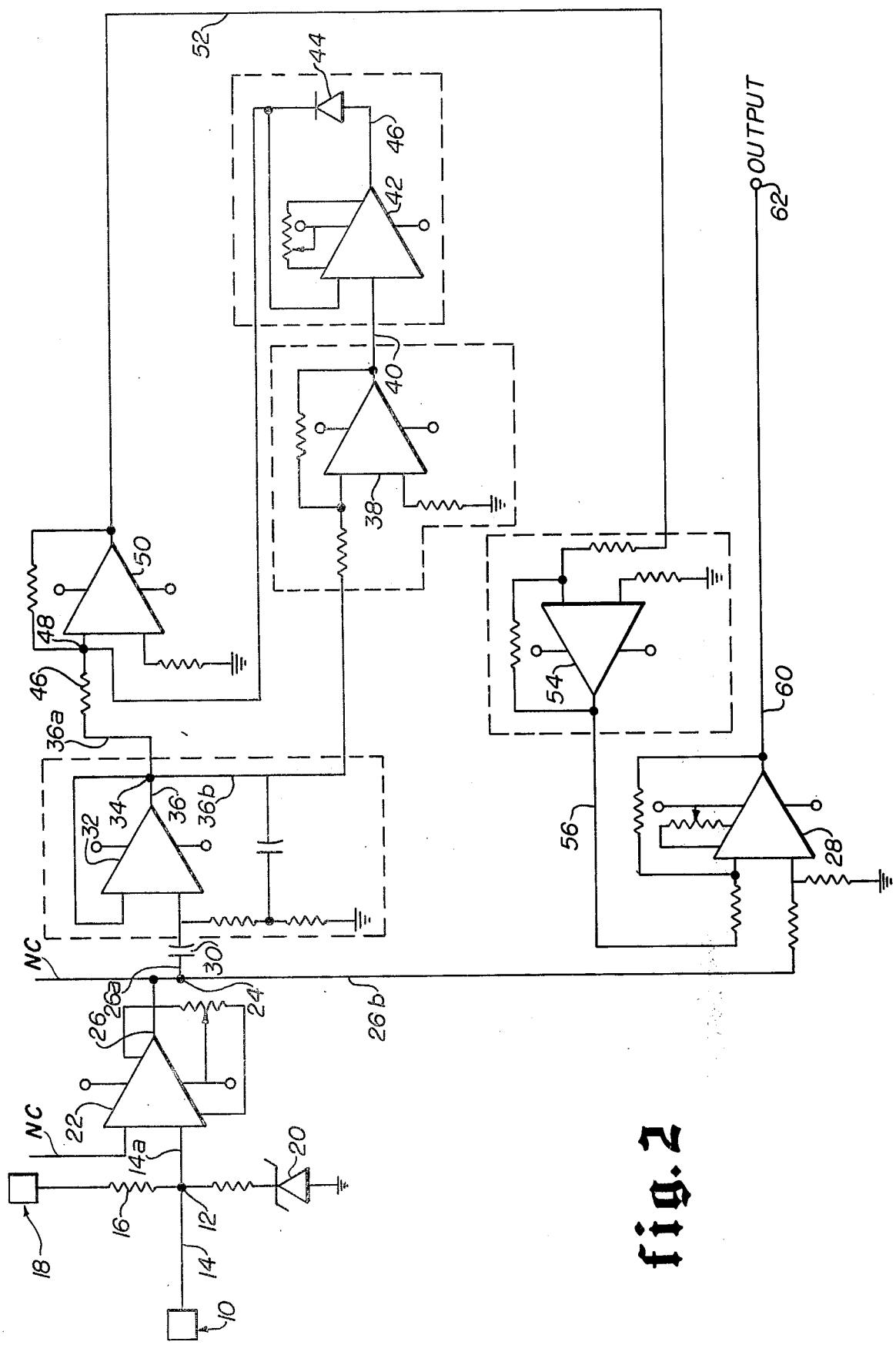
FIG. 2 is a schematic illustration of an electrical circuit of the present invention.

The circuit of the present invention for enabling such a precise determination under continuous operating condition is schematically illustrated in FIG. 2. The continuously sensing reference electrode 10 is disposed in the protection system electrolyte at a predetermined location and is electrically conducted to an electrical junction 12 by electrical conductor 14 in the usual manner. Electrically connected with the junction 12 is a resistor 16 which is in turn connected with a source 18 of positive direct current at a relatively low voltage to ensure a reference voltage reading at electrical junction 12 if the reference electrode 10 should fail for some reason. The central junction 12 is also connected to system ground through a Zener diode 20 to provide overload protection for the reference electric circuit in the event a voltage surge is sensed by the reference electrode 10 which would damage the buffer amplifier 22 which has its input connected to the central junction 12 by conductor 14a.

Figure 3:
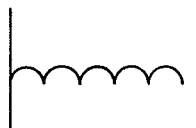
FIGS. 3-6 are illustrative of typical wave forms at various locations in the circuit of FIG. 2.

The purpose of the input buffer amplifier 22 is to strengthen the electrolyte input signal from the reference electrode 10 to a usable signal level and protect the circuit of the present invention from voltage surges of input signal which could possibly damage the circuit. A suitable amplifier for this input buffer amplifier purpose is the model 536 available from Signetics Corporation of Sunnyvale, Calif. The output signal from the buffer amplifier 22 as illustrated in FIG. 3 includes the natural reference voltage component and a pulsing or rippling component formed by the IR drop in the electrolyte.

The output signal of the buffer amplifier 22 is conducted to electrical junction 24 through electrical conductor 26. At the electrical junction 24, the output signal of the buffer amplifier 22, which is the two component signal sensed voltage by the reference electrode 10, is separated into the conductive paths for processing before being recombined algebraically to produce an electrical signal representing the true polarization or reference voltage at the reference electrode 10.

Extending from the electrical junction 24 are electrical conductors 26a and 26b with the conductor 26b electrically connected to summing amplifier 28 for supplying the two component reference voltage signal to amplifier 28 for a purpose to be described more fully hereinafter.

Figure 4:
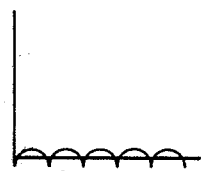

Electrically mounted in the conductor 26a is a capacitor 30 which serves as a direct current filter for eliminating the true natural reference direct current voltage component from the output signal of the buffer amplifier 22. The IR drop signal component passes through the capacitor 30 and conductor 26a to a unity gain buffer amplifier 32. The input signal to the buffer amplifier 32 is therefore the alternating current portion or component of the reference cell voltage that is provided by the IR voltage drop and is of both positive and negative polarity as illustrated in FIG. 4.

The unity gain amplifier 32 serves as a buffer for the electrical components downstream of the DC filter provided by the capacitor 30. A suitable general purpose operational amplifier for use throughout the circuit of FIG. 2, with the exception of buffer amplifier 22, is a Signetics Model uA741 linear integrated circuit that is commercially available from Signetics Corporation of Sunnyvale, Calif. and which is illustrated and described at pages 6–131 through 6–134 of their catalog. The output signal from the buffer amplifier 32 is conducted to electrical junction 34 through conductor 36 which branches at junction 34 into electrical conductors 36a and 36b.

The electrical conductor branch 36b is connected to the input to an inverting amplifier 38. The reversed polarity AC output of the inverting amplifier 38 is connected by an electrical conductor 40 to a rectifier 42 whose DC output signal is passed through diode 44 in the output conductor 46 to produce precision rectification inverted from the polarity of the AC input signal and is equal to the RMS value of the AC input. After passing through the protective diode 44 the precision rectified DC output signal is recombined with the AC output signal from buffer amplifier 32 in the conductor 36a downstream of fixed resistor 46 at electrical junction 48.

Figure 5:
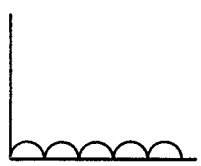
Figure 6:
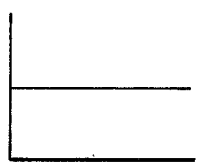

The direct current output of the precision rectifier 42 is combined with the alternating current signal from the buffer amplifier 32 at junction 48 to produce an added electrical signal of constant polarity as illustrated in FIG. 5. The added signal of constant polarity is then amplified in the amplifier 50 to a usable signal level and which reflects the alternating current or IR component or portion of the reference voltage signal sensed by the reference electrode 10. This AC signal is conducted through conductor 52 to the summing amplifier 28 after passing through inverting amplifier 54 and conductor 56. The inverting amplifier 54 assures that the summing amplifier 28 recombines the input signals algebraically. The summing amplifier 28 sums the difference between the entire reference voltage signal input received through conductor 26b and the IR voltage component input received through conductor 52. Within the summing amplifier the IR voltage component is used to reduce the reference cell voltage signal by that component with resulting output signal through conductor 60 being the true cathode or reference potential. This output is electrically connected through conductor to a suitable junction 62 for either indicating visually the magnitude of the reference voltage or for use as an automatic control feed back signal for the source of impressed current or both.

Operation

The method and apparatus of the present invention may be used to determine the true reference voltage in any electrolyte where undesired corrosion exists or may occur. Such use may be to simply measure the reference voltage for informational purposes or may be used as an automatic control signal. Whatever the particular use, the reference electrode is placed at a predetermined location in the electrolyte after the apparatus has been properly connected.

After the power supply for the circuit is activated, the true cathodic polarization potential signal will be available at the terminal 62. Such signal is developed by processing in the previously disclosed manner within the circuit and the output signal at terminal 62 is useful in automatic control for an impressed current corrosion protection systems.

The foregoing disclosure and description of the invention are illustrative and explanatory thereof, and various changes in the size, shape and materials as well as in the details of the illustrated construction may be made without departing from the spirit of the invention.

I claim:

1. A method of continuously determining the natural reference voltage in an impressed current corrosion protection system having cyclic pulses of direct current for retarding undesired corrosion including the steps of:
   sensing continuously the voltage present in the electrolyte of the corrosion protection system with a reference electrode;
   producing a continuous electrical signal as a function of the sensed voltage;
   passing the electrical signal into two separate conductive paths;
   conducting the electrical signal in one conductive path to a summing amplifier without change to the electrical signal;
   filtering the direct current voltage from the electrical signal through a capacitor in the second conductive paths to provide a resulting electrical signal that is a function of the fluctuating voltage drop of the sensed impressed current resistance of the corrosion protection system;
   amplifying the filtered electric signal that is a function of the fluctuating voltage drop of the impressed current resistance to provide an electrical signal of a constant polarity in the second conductive path;
   inverting the filtered and amplified electrical signal of a constant polarity in the second conductive path; and
   combining the separate signals in the two conductive paths algebraically at the summing amplifier to obtain an output signal from the summing amplifier that is a function of only the natural reference voltage of the cathodic protection system.

* * * * *